United States Patent
Wang et al.

(10) Patent No.: US 11,666,516 B2
(45) Date of Patent: Jun. 6, 2023

(54) AQUEOUS ORAL CARE THIOCYANATE-CONTAINING COMPOSITIONS, METHODS, AND KITS

(71) Applicant: 3M INNOVATIVE PROPERTIES COMPANY, St. Paul, MN (US)

(72) Inventors: Yizhong Wang, Woodbury, MN (US); Ta-Hua Yu, Woodbury, MN (US); Joel D. Oxman, Minneapolis, MN (US); Richard P. Rusin, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 316 days.

(21) Appl. No.: 17/250,351

(22) PCT Filed: Jul. 25, 2019

(86) PCT No.: PCT/IB2019/056377
§ 371 (c)(1),
(2) Date: Jan. 8, 2021

(87) PCT Pub. No.: WO2020/021495
PCT Pub. Date: Jan. 30, 2020

(65) Prior Publication Data
US 2021/0290501 A1    Sep. 23, 2021

Related U.S. Application Data

(60) Provisional application No. 62/703,976, filed on Jul. 27, 2018.

(51) Int. Cl.
| | | |
|---|---|---|
| *A61K 8/21* | (2006.01) | |
| *A61K 8/46* | (2006.01) | |
| *A61Q 11/00* | (2006.01) | |
| *A61Q 11/02* | (2006.01) | |

(52) U.S. Cl.
CPC .............. *A61K 8/21* (2013.01); *A61K 8/46* (2013.01); *A61Q 11/00* (2013.01); *A61Q 11/02* (2013.01); *A61K 2800/5424* (2013.01); *A61K 2800/5426* (2013.01); *A61K 2800/92* (2013.01)

(58) Field of Classification Search
CPC . A61Q 11/00; A61K 8/19; A61K 6/00; A61K 8/20
USPC .............................. 424/49, 52, 618, 609, 607
IPC ....................................................... A61Q 11/00
See application file for complete search history.

(56) References Cited

U.S. PATENT DOCUMENTS

| | | | |
|---|---|---|---|
| 4,012,839 A | 3/1977 | Hill | |
| 6,461,161 B1 | 10/2002 | Ngo | |
| 8,968,709 B2 | 3/2015 | Yang | |
| 2002/0156130 A1 | 10/2002 | Melman | |

FOREIGN PATENT DOCUMENTS

| | | |
|---|---|---|
| WO | WO 2018-092889 | 5/2018 |
| WO | WO 2019-155358 | 8/2019 |
| WO | WO 2020-021494 | 1/2020 |

OTHER PUBLICATIONS

Ashby et al., "Inorganic Chemistry of Defensive Peroxidases in the Human Oral Cavity." J Dent Res 87(10):900-914, 2008. (Year: 2008).*

International Search Report for PCT International Application No. PCT/IB2019/056377, dated Nov. 22, 2019, 4 pages.

* cited by examiner

*Primary Examiner* — Walter E Webb
(74) *Attorney, Agent, or Firm* — 3M Innovative Properties Company

(57) ABSTRACT

An aqueous oral care one-part composition (e.g., solution), a kit that includes such composition (e.g., solution), and methods (e.g., a method of providing fluoride to a patients tooth surface), wherein the oral care composition (e.g., solution) includes: silver cations; thiocyanate anions; fluoride anions; and water.

10 Claims, No Drawings

AQUEOUS ORAL CARE THIOCYANATE-CONTAINING COMPOSITIONS, METHODS, AND KITS

CROSS REFERENCE TO RELATED APPLICATIONS

This application is a national stage filing under 35 U.S.C. 371 of PCT/IB2019/056377, filed Jul. 25, 2019, which claims the benefit of U.S. Provisional Application No. 62/703,976, filed Jul. 27, 2018, the disclosure of which is incorporated by reference in its/their entirety herein.

BACKGROUND

Silver and fluoride ions are well-known for treating tooth surfaces to address hypersensitivity and arrest dental caries.

Fluoride treatment involves the application of fluoride to a tooth surface with the formation of fluorapatite and calcium fluoride. There are two major in-office fluoride treatment methods currently in use.

One treatment method uses a fluoride gel/foam in a tray. This method requires several grams of fluoride gel stored in a tray that is then placed into a patient's mouth onto the teeth. This tray is left in the mouth with the gel/foam in contact with the teeth for 1 to 4 minutes. The gel/foam formulation is an aqueous system that includes 2% sodium fluoride. This material requires the use of suction to pull the extra gel out of the mouth to avoid unnecessary high amounts of fluoride ingestion.

Another treatment method is a dental fluoride varnish. Most fluoride varnishes on the market are rosin/ethanol based formulations with a hydrophobic nature. The varnish is painted on the teeth and remains in place for several hours to allow for the fluoride to be released from the composition. Typically, dentists use fluoride varnishes for in-office fluoride treatment. Most dental fluoride varnishes include 5% sodium fluoride. The dose of varnish is about 0.5 gram. Dental varnishes place much smaller amounts of fluoride into a patient's mouth compared to fluoride gel/foams. Thus, fluoride ingestion is less with fluoride varnishes. Also, fluoride varnishes are easier to apply as they are simply painted on a patient's teeth; however, fluoride varnish treatments are more labor intensive than gel treatments and fluoride varnish treatments leave the patient with an unpleasant "dirty teeth" feeling.

Stable aqueous solutions containing both silver and fluoride ions are needed. One such solution includes silver diamine fluoride (SDF); however, SDF is also known for turning the tooth surface black when it is exposed to light.

Compositions that are as simple to apply to teeth as varnishes and work in time periods as short as gel/foam formulations are desired, particularly those compositions that include silver and fluoride, but do not stain the tooth surface upon exposure to light.

SUMMARY OF THE DISCLOSURE

The present disclosure provides aqueous oral care compositions (e.g., solutions) and methods of treating (e.g., methods of providing fluoride to a patient's tooth surface). Such compositions are one-part compositions.

Such one-part compositions (e.g., solutions) can be used as in-office oral care solutions (e.g., as fluoride treatment solutions). They can be formulated into a solution that can be painted on a tooth surface if desired. They can provide similar fluoride efficacy to that of varnishes in the shorter periods of time of gel/foam formulations.

In one embodiment, the present disclosure provides an aqueous oral care one-part composition (e.g., solution) that includes: silver cations; thiocyanate anions; fluoride anions; and water.

In certain embodiments, the molar ratio of silver to thiocyanate ions is less than 0.37:1, and water is less than 57.1 wt-%, based on the total weight of the composition (e.g., solution). In certain embodiments, the molar ratio of silver to thiocyanate ions is at least 0.1:1 and less than 0.37:1.

In certain embodiments, the oral care composition (e.g., solution) forms a precipitate (e.g., AgSCN) upon contact with additional water or saliva.

In certain embodiments of such embodiments, an aqueous oral care one-part composition (e.g., solution) includes: 12.2-20 wt-% silver cations; and 2.0-4.0 wt-% fluoride anions; wherein the weight percentages are based on the total weight of the composition (e.g., solution). In another embodiment, the present disclosure provides a method of providing fluoride to a patient's tooth surface. The method involves applying an aqueous oral care one-part composition (e.g., solution) as disclosed herein to the patient's tooth surface.

In another embodiment, the present disclosure provides a method of reducing the incidence of dental caries. The method involves applying an aqueous oral care one-part composition (e.g., solution) as disclosed herein to the patient's tooth surface.

In another embodiment, the present disclosure provides a method of reducing dentin sensitivity and/or root sensitivity (e.g., during cavity treatment and/or on an exposed root) in a patient in need thereof. The method involves applying an aqueous oral care one-part composition (e.g., solution) as disclosed herein to the patient's tooth surface.

In another embodiment, the present disclosure provides a method of treating a patient's tooth surface. The method involves applying an aqueous oral care one-part composition as disclosed herein to the patient's tooth surface. In certain embodiments, the method further includes applying a dental restorative to the treated tooth surface.

In another embodiment, the present disclosure provides a kit that includes an aqueous oral care one-part composition (e.g., solution) as described herein and an applicator.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

The present disclosure provides aqueous oral care compositions (e.g., solutions). Such compositions are one-part compositions.

The present disclosure also provides methods, such as providing fluoride to a patient's tooth surface, as well as reducing the incidence of dental caries, for example. Such methods involve applying an aqueous oral care one-part composition (e.g., solution such as a fluoride treatment solution) as described herein to the patient's tooth surface.

In certain embodiments, applying an aqueous oral care one-part composition (e.g., solution) includes painting the oral care one-part composition (e.g., solution) on the patient's tooth surface.

In certain embodiments, applying an aqueous oral care one-part composition (e.g., solution) includes dispensing the oral care one-part composition (e.g., solution) into a dental tray and attaching the tray having the oral care one-part composition (e.g., solution) therein to the patient's tooth surface. In certain embodiments, the dental tray includes an orthodontic aligner treatment tray.

In certain embodiments, an aqueous oral care one-part composition (e.g., solution) includes: silver cations; thiocyanate anions; fluoride anions; and water.

In certain embodiments, the silver ions (also referred to herein as silver cations) are present in an amount of at least 12.2 percent by weight (wt-%), at least 13 wt-%, or at least 13.5 wt-%, wherein the weight percentages are based on the total weight of the composition (e.g., solution). In certain embodiments, the silver cations are present in an amount of up to 20 wt-%, up to 19 wt-%, up to 18 wt-%, or up to 17 wt-%, wherein the weight percentages are based on the total weight of the composition (e.g., solution).

In certain embodiments, the source of silver cations is selected from silver fluoride, silver chloride, silver nitrate, silver iodide, silver diamine fluoride, and combinations thereof.

In certain embodiments, the fluoride ions (also referred to herein as fluoride anions) are present in an amount of at least 2.0 wt-%, at least 2.1 wt-%, at least 2.2 wt-%, or at least 2.25 wt-%, wherein the weight percentages are based on the total weight of the composition (e.g., solution). In certain embodiments, the fluoride anions are present in an amount of up to 4.0 wt-%, up to 3.9 wt-%, up to 3.8 wt-%, up to 3.5 wt-%, or up to 3.0 wt-%, wherein the weight percentages are based on the total weight of the composition (e.g., solution).

In certain embodiments, the source of fluoride anions is selected from silver fluoride, silver diamine fluoride, sodium fluoride, ammonium fluoride, potassium fluoride, amine fluoride, and combinations thereof.

In certain embodiments, an aqueous oral care one-part composition (e.g., solution) includes: 12.2-20 wt-% silver cations; and 2.0-4.0 wt-% fluoride anions; wherein the weight percentages are based on the total weight of the composition (e.g., solution). In certain embodiments, the oral care one-part composition (e.g., solution) includes: 12.2-20 wt-% silver cations; and 2.2-3.5 wt-% fluoride anions.

In certain embodiments, the molar ratio of silver to thiocyanate ions is less than 0.37:1. In certain embodiments, the molar ratio of silver to thiocyanate ions is at least 0.1:1.

In certain embodiments, the source of thiocyanate ions (also referred to herein as thiocyanate anions) is selected from ammonium thiocyanate, sodium thiocyanate, potassium thiocyanate, guanidinium thiocyanate, and combinations thereof.

In certain embodiments, iodide is also present. In certain embodiments, if iodide is present in addition to thiocyanate, the molar ratio of silver to iodide ions is less than 0.42:1. In certain embodiments, if iodide is present in addition to thiocyanate, the molar ratio of silver to iodide ions is at least 0.09:1. In certain embodiments, the source of iodide ions (also referred to herein as iodide anions) is selected from ammonium iodide, sodium iodide, potassium iodide, silver iodide, and combinations thereof.

In certain embodiments, an aqueous oral care one-part composition (e.g., solution) includes water in an amount of at least 20 wt-%, based on the total weight of the composition (e.g., solution).

In certain embodiments, the amount of water is less than 57.1 wt-%, based on the total weight of the composition (e.g., solution).

Upon contact with additional water or saliva in the oral environment, the oral care one-part composition (e.g., solution) forms a precipitate (i.e., a solid formed from the composition (e.g., solution)). The precipitate includes AgSCN, which provides antibacterial effect.

In certain embodiments, an oral care one-part composition (e.g., solution) includes: 12.2-20 wt-% silver cations; and 2.0-4.0 wt-% (or 2.2-3.5 wt-%) fluoride anions; wherein the weight percentages are based on the total weight of the composition (e.g., solution); and thiocyanate anions, wherein a molar ratio of silver to thiocyanate ions is at least 0.1:1 and less than 0.37:1; wherein the oral care one-part composition (e.g., solution) forms a precipitate upon contact with additional water or saliva.

Oral care one-part compositions (e.g., solutions) of the present disclosure are aqueous compositions (e.g., solutions), although they may include a small amount of one or more organic solvents. Examples of organic solvents are selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Preferably, the aqueous oral care one-part compositions (e.g., solutions) are free of organic solvents that function as liquid carriers (as opposed to organic solvents that are used as carriers/solvents for flavorants or sweeteners). For example, certain additives may be provided as a solution or dispersion in an organic solvent as a liquid carrier. If there is any organic solvent (that functions as a liquid carrier) present in aqueous oral care one-part compositions (e.g., solutions) of the present disclosure, it is present in an amount of less than 5 wt-%, based on the total weight of the aqueous composition (e.g., solution).

Preferably, aqueous oral care one-part compositions (e.g., solutions) of the present disclosure do not stain teeth, which is particularly surprising because of the potential oxidation of silver. This can be determined by combining an oral care composition (e.g., solution) in a ratio of 3:1 with a 1% phosphate solution and exposing it to a blue LED light with wavelength of 430-480 nm and output of approximately 1500 mW/cm$^2$ (−10%/+20%), such as that commercially available under the Tradename 3M ELIPAR DEEPCURE-S LED curing light (available from 3M Company, St. Paul, Minn.), for 20 seconds to see whether the mixture forms a dark (e.g., black, brown, or grey) precipitate.

Significantly, compositions (e.g., solutions) of the present disclosure do not turn (discolor) to a dark color such as black, brown, or grey after being precipitated and exposed to LED light. While not being bound by theory, it is believed that the AgSCN, fluoride ions, and excess thiocyanate ions, complex with calcium in the tooth, and thereby avoid discoloration.

Preferably, aqueous oral care compositions of the present disclosure are solutions that are shelf stable for at least 6 months, or at least 1 year without precipitation (detectable to the human eye particularly when in a sealed container. Thus, aqueous oral care solutions of the present disclosure are clear (i.e., transparent or translucent without any cloudiness) for at least 6 months, or at least 1 year until contacted with additional water or saliva.

Additional Optional Active Agents

Aqueous oral care one-part compositions (e.g., solutions) of the present disclosure can also contain one or more active agents in addition to a source of fluoride. When included, the one or more additional active agents usually, but not always, include one or more active agents that are active in the oral cavity against disorders, diseases, or conditions of the teeth, gums, cheeks, tongue, roof of the mouth, and the like.

Examples of additional active agents that can be employed include one or more other fluorine-containing compounds, such as sodium monofluorophosphate, stannous fluoride, calcium fluoride, strontium fluoride, zinc fluoride, zinc potassium fluoride, ammonium fluoride, potassium magnesium fluoride, and combinations thereof.

Examples of additional active agents that can be employed include one or more whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, and proteins. Various combinations of such additional active agents may be used if desired. When employed, one or more additional active agents will be typically used in amounts sufficient to achieve their intended effect.

When employed, the whitening agents can be a wide variety of suitable whitening agents. The whitening agents can include, for example, a peroxide whitening agent, a non-peroxide whitening agent, or both. Peroxide whitening agents include hydrogen peroxide, peroxide of alkali or alkaline earth metals, such as sodium peroxide, potassium peroxide, lithium peroxide, magnesium peroxide, calcium peroxide, barium peroxide, and the like, glyceryl hydrogen peroxide, alkyl hydrogen peroxide, dialkyl peroxide, peroxy acids or peroxy acid salts, benzoyl peroxide, urea peroxide, and the like. Hydrogen peroxide is most common. Non-peroxide whitening agents include chlorine dioxide, chlorites, and hypochlorites. Chlorites and hyperchlorites are typically in the form of alkali or alkaline earth metal salts, such as salts of lithium, potassium, sodium, magnesium, calcium, or barium. Colorants, titanium dioxide, and hydroxyapatite can also be used.

When employed, the anticalculus agents can be a wide variety of suitable anticalculus agents. The anticalculus agents can include, for example, phosphates, polyphosphates, such as pyrophosphates, polyolefin sulfonates, polyolefin phosphates, diphosphonates, phosphonoalkane carboxylic acids, and salts thereof, typically alkali metal or ammonium salts.

When employed, the remineralization agents can be a wide variety of suitable remineralization agents. The remineralization agents can include, for example, materials that release calcium ions, phosphorous-containing ions, or both, such as calcium phosphate (e.g., mono-, di-, and/or tricalcium phosphate), hydroxyapatite, calcium carbonate, and the like.

Examples of materials that release calcium ions are calcium salts that are water soluble, such as those selected from calcium chloride, calcium nitrate, calcium gluconate, calcium lactate gluconate, calcium acetate, hydrates thereof, and combinations thereof. In certain embodiments, the calcium salt is selected from calcium chloride, calcium nitrate, hydrates thereof, and combinations thereof.

A calcium salt can also be used to modulate the fluoride release profile.

When employed, the stannous sources can be a wide variety of suitable sources of stannous ions. The stannous ion sources can include, for example, stannous halides, organic stannous carboxylate salts, such as stannous formate, stannous acetate, stannous gluconate, stannous lactate, stannous tartrate, and stannous citrate. When the fluoride source is stannous fluoride, it can also function as a stannous source.

When employed, the antimicrobial agents can include a wide variety of orally acceptable antimicrobial agents. Examples include triclosan, 8-hydroxyquinoline, zinc ion, stannous ion, cupric compounds, phthalic acid and salts thereof, quaternary ammonium compounds, sanguinarine, salicylanilide, salicylic acid, thymol, eugenol, neomycin, kanamycin, clindamycin, amoxicillin, tetracycline, doxycycline, minocycline, metronidazole, chlorohexidine, and the like.

When employed, the antioxidants can be a wide variety of orally acceptable antioxidants. Examples include butylated hydroxy anisone, butylated hydroxy toluene, vitamin A, carotenoids, vitamin E, flavonoids, polyphenols, ascorbic acid or salts thereof, chlorophyll, melatonin, and the like.

When employed, the saliva stimulants can be a wide variety of orally acceptable saliva stimulants. Examples include citric acid, lactic acid, succinic acid, ascorbic acid, adipic acid, fumaric acid, and tartaric acid.

When employed, the breath freshening agents can be a wide variety of orally acceptable breath freshening agents. Examples include zinc salts such as zinc salts of gluconate, citrate, chlorite, alpha-ionone, and the like.

When employed, the antiplaque agents can be a wide variety of orally acceptable antiplaque agents. Examples include stannous salts, salts of copper, magnesium or strontium, dimethicone copolyols, such as cetyl dimethicone copolyol, papain, glucoamylase, glucose oxidase, urea, calcium lactate, calcium glycerophosphate, strontium polyacrylates, and the like. Further examples of antiplaque agents include biofilm inhibition agents, particularly those described in U.S. Pat. No. 8,968,709 (Yang et al.).

When employed, the anti-inflammatory agents can be a wide variety of orally acceptable anti-inflammatory agents. Examples include steroids such as fluocinolone and hydrocortisone, non-steroidal anti-inflammatory drugs such as ketorolac, flurbiprofen, ibuprofen, naproxen, indomethacin, diclofenac, etodolac, indomethacin, sulindac, tolmetin, ketoprofen, fenoprofen, piroxicam, nabumetone, acetyl salicylic acid, salicylic acid, diflunisal, meclofenamate, mefenamic acid, oxyphenbutazone, phenylbutazone, and the like.

When employed, the $H_2$ antagonists can be a wide variety of orally acceptable $H_2$ antagonists. Examples include cimetidine, etinidine, ranitidine, tiotidine, lupitidine, denetidine, famotidine, roxatidine, pifatidine, lamtidine, zaltidine, nizatidine, mifentidine, ramixotidine, loxtidine, bisfentidine, sufotidine, ebrotidine, impromdine, and the like.

When employed, the desensitizing agents can be a wide variety of orally acceptable desensitizing agents. Examples include potassium citrate, potassium chloride, potassium tartrate, potassium bicarbonate, potassium oxalate, potassium nitrate, strontium salts, arginine, acetyl salicylic acid or salts thereof, salicylic acid or salts thereof, codeine, acetaminophen, and the like.

When employed, the nutrients can be a wide variety of orally acceptable nutrients. Examples include vitamins, such as vitamins C, D, thiamine, riboflavin, folic acid, nicotinamide, niacin, pyridoxine, bioflavonoids, and the like, supplements, such as amino acids, lipotropics, fish oil, polyunsaturated fatty acids, eicosapentaenoic acid, docosahexanoic acid, coenzyme Q10, ubiquinone, minerals such as potassium, and the like.

When employed, the proteins can include a wide variety of orally acceptable proteins. Examples include milk proteins, peroxide producing enzymes, amylase, papain, glucoamylase, glucose oxidase, and the like.

Buffers

Aqueous oral care one-part compositions (e.g., solutions) of the present disclosure can include a pharmaceutically acceptable buffer. The type and amount of such buffer is selected to provide an oral care composition (e.g., solution) with a pH of at least 5.5, at least 6, or at least 6.5. In certain embodiments, the type and amount of such buffer is selected to provide an oral care composition (e.g., solution) with a pH of up to 9, up to 8.5, up to 7.5, or up to 7. In certain embodiments, the type and amount of such buffer is selected to provide an oral care composition (e.g., solution) with a pH of 6.5 to 7.5, or a pH of 7.0. A wide variety of suitable pharmaceutically acceptable buffers can be included. Examples include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, tris(hydroxymethyl)-aminomethane, or mixtures thereof.

Thickeners

In certain embodiments, aqueous oral care one-part compositions (e.g., solutions) of the present disclosure include a thickener to provide a composition (e.g., solution) with a suitable viscosity to allow for the desired method of application. For example, a suitable thickener in a sufficient amount may be used to achieve a composition (e.g., solution) viscosity adequate to maintain the composition (e.g., solution) in an inverted mouthpiece tray applicator for up to four minutes (typical time for a professionally applied fluoride treatment), and yet be fluid enough to have acceptable handling characteristics for the dental operator (e.g., when dispensing into a dental tray applicator). Or, a suitable thickener in a sufficient amount may be used to achieve a viscosity adequate to paint on a tooth surface.

In certain embodiments, the type and amount of thickener is selected to provide an oral care composition (e.g., solution) with a viscosity of at least 0.5 Pascal seconds at a shear rate of 1.0/second. In certain embodiments, a type and amount of thickener is selected to provide an oral care composition (e.g., solution) with a viscosity of up to 500 Pascal seconds at a shear rate of 1.0/second.

In certain embodiments, a thickener is present in an oral care one-part composition (e.g., solution) in an amount of less than 2.5 wt-%, based on the total weight of the aqueous composition (e.g., solution). In certain embodiments, a thickener is present in an amount of at least 0.5 wt-%, based on the total weight of the aqueous composition (e.g., solution).

Suitable thickeners are typically those that are generally safe for human ingestion (FDA approved for internal use), do not bind fluoride ions, and do not significantly affect the bioavailability of fluoride ions.

In certain embodiments, the thickener is selected from natural gums, non-acid cellulose derivatives (e.g., hydroxyethyl cellulose), inorganic fillers (e.g., colloidal silica, fumed silica, alumina, titania, and zinc oxide), alkylene oxide polymers (e.g., polyethylene glycol, polypropylene glycol, and copolymers of polyethylene glycol and polypropylene glycol), non-acid modified starches, and combinations thereof.

Optional Additives

In certain embodiments, aqueous oral care compositions (e.g., solutions) of the present disclosure include one or more optional additives including flavoring agents (i.e., flavorants) and sweeteners. Other optional additives include surfactants. Various combinations of such additives may be used if desired.

In certain embodiments, aqueous oral care compositions (e.g., solutions) of the present disclosure include a sweetener. A wide variety of orally acceptable sweeteners can be used. Common sweeteners include xylitol, sorbitol, sucralose, aspartame, saccharin, usually sodium saccharine, and the like. When present, a sweetener can be used in any suitable amount, most often in an amount sufficient to impart a pleasant sweetness to the composition (e.g., solution). The suitable amount is typically 0.5 wt-% to 15 wt-%, based on the total weight of the aqueous composition (e.g., solution).

In certain embodiments, aqueous oral care compositions (e.g., solutions) of the present disclosure include a flavoring agent. A wide variety of orally acceptable flavoring agents can be used. Common flavoring agents include peppermint oil, spearmint oil, cherry flavor, citric acid, orange flavor, vanilla, strawberry flavor, coconut flavor, and bubble gum flavor. When present, a flavoring agent can be used in any suitable amount, most often in an amount sufficient to impart a desired flavor to the composition (e.g., solution). The suitable amount is typically 1 wt-% to 4 wt-%, based on the total weight of the aqueous composition (e.g., solution).

In certain embodiments, aqueous oral care compositions (e.g., solutions) of the present disclosure include a surfactant. Typically, such surfactant is an anionic surfactant, examples of which include polysorbate, glycerol, polyglycerol-based surfactant, or combinations thereof. When present, a surfactant can be used in any suitable amount, most often in an amount sufficient to impart wettability. A suitable amount is typically 0.1 wt-% to 5.0 wt-%, based on the total weight of the aqueous composition (e.g., solution).

Kits

In certain embodiments, aqueous oral care compositions (e.g., solutions) of the present disclosure are included in kits. Typically, such kit includes an applicator (e.g., dental brush, cotton tip swab) for the oral care composition (e.g., solution). Such applicator may be integrated into a container having the oral care composition (e.g., solution) therein.

In certain embodiments, the oral care composition (e.g., solution) is provided in individual sealed unit dose containers. In use, the seals of such individual sealed unit dose containers are broken and the composition (e.g., solution) picked up with the applicator and the composition (e.g., solution) applied to a tooth surface.

In certain embodiments, the oral care composition (e.g., solution) is provided in a multi-dose container. In use, a drop of the composition (e.g., solution) can be dispensed onto a tray, piece of plastic, piece of paper, dish, well, pan, etc., and the composition (e.g., solution) picked up with the applicator and the composition (e.g., solution) applied to a tooth surface.

In certain embodiments, the kit may further include one or more of a dental restorative, a tray, a dish, a well, or a pan. Examples of dental restorative include, but are not limited to, an adhesive, primer, cement, liner, sealant, amalgam, resin, resin composite, glass ionomer, resin-modified glass ionomer, glass-ceramic, ceramic, metal, plastic, or combination thereof.

Methods of Making and Using

An aqueous oral care composition (e.g., solution) of the present disclosure can be made using any techniques known to one of skill in the art. In certain embodiments, the components are added together into water and dissolved, in no particular order. Alternatively, the order of addition can be important in obtaining a composition (e.g., solution). For example, in certain embodiments, the source(s) of silver and fluoride (e.g., AgF) is dissolved in water first and then the source of thiocyanate (and optionally, a source of iodide) is added. Alternatively, each component can be dissolved in water separately and then combined to form an aqueous oral care composition (e.g., solution).

In certain embodiments, an aqueous oral care composition (e.g., solution) of the present disclosure is used in a method of providing fluoride to a patient's tooth surface. The method includes applying the aqueous oral care composition (e.g., solution) described herein to the patient's tooth surface.

In certain embodiments, an aqueous oral care composition (e.g., solution) of the present disclosure is used in a method of reducing the incidence of dental caries (e.g., by preventing or arresting dental caries) in a patient in need thereof. The method includes applying the aqueous oral care composition (e.g., solution) described herein to the patient's tooth surface.

In certain embodiments, an aqueous oral care composition (e.g., solution) of the present disclosure is used in a method of reducing dentin sensitivity and/or root sensitivity (e.g., during cavity treatment and/or on an exposed root) in a patient in need thereof. The method includes applying the aqueous oral care composition (e.g., solution) described herein to the patient's tooth surface.

In certain embodiments, an aqueous oral care composition (e.g., solution) of the present disclosure is used in a method of treating a patient's tooth surface. The method includes applying the aqueous oral care one-part composition (e.g., solution) disclosed herein to the patient's tooth surface to form a treated tooth surface, and optionally applying a dental restorative to the treated tooth surface.

In certain embodiments, a patient's tooth surface that is treated with a method as described herein includes enamel, dentin, cementum, root, or combinations thereof.

In certain embodiments of the methods described above, applying includes painting the oral care composition (e.g., solution) on the patient's tooth surface. In certain embodiments of the methods described above, applying includes dispensing the oral care composition (e.g., solution) into a dental tray (e.g., an orthodontic aligner treatment tray) and attaching the tray having the oral care composition (e.g., solution) therein to the patient's tooth surface.

In certain embodiments of the methods described above, the oral care composition (e.g., solution) is subsequently dried (e.g., using flowing air) after being applied to the tooth surface. The source of flowing air can be delivered from an air compressor that delivers at high pressure limits of 115 psi. One example of a suitable air compressor is an Osprey Compressor from RAMVAC (models OSP22, OSP13, OSP23, OSP24, OSP25, OSP28) commercially available from Dental EZ Integrated Solutions of Malvern, Pa., or Patterson Dental of St. Paul, Minn. Another example of an air compressor is AirStar Neo air compressors by AIR TECHNIQUES (Models such as AirStar 10 Neo, AirStar 21 Neo) commercially available from Patterson Dental of St. Paul, Minn. Alternatively, the pressurized gas device could be a typical air/water syringe found in most dental offices for delivering pressurized air. Optimum air pressure with a typical dental air/water syringe is 40-80 psi. Such syringes are used to dry the teeth or to blow scaled calculus off the teeth. One example of such a syringe is a Johnson-Promident 3-Way Air/Water Syringe commercially available from Patterson Dental Supply Inc., Patterson Item #: 404-1893. Regardless, the gas is blown by some pressurized gas source, and could be air or some other inert gas or gas mixture. For example, the gas could be nitrogen, helium, argon, carbon dioxide, or nitrous oxide. The source of pressurized gas could be part of a permanently installed "in-house" pressurized air/gas system or a hand held, self-contained canister.

In certain embodiments of the methods described above, water is subsequently applied to the oral care composition (e.g., solution) after being applied to the tooth surface to form a precipitate thereon (i.e., on the tooth surface). In certain embodiments of the methods described above, saliva is subsequently allowed to contact the oral care composition (e.g., solution) on the tooth surface to form a precipitate thereon (i.e., on the tooth surface).

In certain embodiments of the methods described herein, the oral care composition (e.g., solution) is subsequently wiped with cotton, paper, and any other wiping material to remove excess oral care composition (e.g., solution) on the tooth surface after being applied to the tooth surface.

In certain embodiments of the methods described above, the methods further include placing a dental restorative on the tooth surface having the oral care composition (e.g., solution) applied thereto (either before or after the composition (e.g., solution) is dried, rinsed off, wiped off, and/or a precipitate is formed on the tooth surface). Examples of dental restorative include, but are not limited to, an adhesive (such as 3M SCOTCHBOND Universal Adhesive (available from 3M Company of St. Paul, Minn., USA), primer, cement (such as 3M RelyX Unicem 2 Automix Self-Adhesive Resin Cement, available from 3M Company of St. Paul, Minn., USA), liner (such as 3M ESPE VITREBOND Plus Light Cure Glass Ionomer Liner/Base), sealant, amalgam, resin, resin composite (3M FILTEK Z250 Universal Restorative), glass ionomer (such as 3M KETAC Universal APLICAP Glass Ionomer Restorative), resin-modified glass ionomer (such as RelyX Luting Plus RMGI Cement), glass-ceramic, ceramic, metal, plastic, or combination thereof.

EXEMPLARY EMBODIMENTS

Embodiment 1 is an aqueous oral care fluoride one-part composition (e.g., solution) comprising: silver cations; thiocyanate anions; fluoride anions; and water.

Embodiment 2 is the oral care composition (e.g., solution) of embodiment 1 wherein the molar ratio of silver to thiocyanate ions is less than 0.37:1.

Embodiment 3 is the oral care composition (e.g., solution) of any of the preceding embodiments wherein the molar ratio of silver to thiocyanate ions is at least 0.1:1.

Embodiment 4 is the oral care composition (e.g., solution) of embodiment 1 or 2 comprising: 12.2-20 wt-% silver cations; and 2.0-4.0 wt-% fluoride anions; wherein the weight percentages are based on the total weight of the composition (e.g., solution).

Embodiment 5 is the oral care composition (e.g., solution) of embodiment 4 comprising: 12.2-20 wt-% silver cations; thiocyanate anions; and 2.2-3.5 wt-% fluoride anions.

Embodiment 6 is the oral care composition (e.g., solution) of any of the preceding embodiments wherein the oral care composition (e.g., solution) forms a precipitate (e.g., AgSCN) upon contact with additional water or saliva.

Embodiment 7 is the oral care composition (e.g., solution) of any of the preceding embodiments comprising a source of silver cations selected from silver fluoride, silver chloride, silver nitrate, silver iodide, silver diamine fluoride, and combinations thereof.

Embodiment 8 is the oral care composition (e.g., solution) of any of the preceding embodiments comprising a source of fluoride anions selected from silver fluoride, silver diamine fluoride, sodium fluoride, ammonium fluoride, potassium fluoride, amine fluoride, and combinations thereof.

Embodiment 9 is the oral care composition (e.g., solution) of any of the preceding embodiments comprising a source of thiocyanate anions selected from ammonium thiocyanate, sodium thiocyanate, potassium thiocyanate, guanidinium thiocyanate, and combinations thereof.

Embodiment 10 is the oral care composition (e.g., solution) of any of the preceding claims further comprising iodide anions.

Embodiment 11 is the oral care composition (e.g., solution) of embodiment 10 wherein the molar ratio of silver to iodide ions is less than 0.42:1, and in certain embodiments at least 0.09:1.

Embodiment 12 is the oral care composition (e.g., solution) of embodiment 10 or 11 comprising a source of iodide anions selected from ammonium iodide, sodium iodide, potassium iodide, silver iodide, and combinations thereof.

Embodiment 13 is the oral care composition (e.g., solution) of any of the preceding embodiments further comprising a pharmaceutically acceptable buffer.

Embodiment 14 is the oral care composition (e.g., solution) of any of the preceding embodiments further comprising a thickener.

Embodiment 15 is the oral care composition (e.g., solution) of embodiment 10 wherein the thickener is present in an amount of less than 2.5 wt-%.

Embodiment 16 is the oral care composition (e.g., solution) of any of the preceding embodiments which has a pH of 5.5 to 9.

Embodiment 17 is the oral care composition (e.g., solution) of any of the preceding embodiments comprising less than 5 wt-% organic solvent.

Embodiment 18 is the oral care composition (e.g., solution) of embodiment 17 wherein the organic solvent is selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Embodiment 19 is the oral care composition (e.g., solution) of any of the preceding embodiments comprising less than 57.1 wt-% water, and in certain embodiments at least 20 wt-% water, based on the total weight of the composition (e.g., solution).

Embodiment 20 is the oral care composition (e.g., solution) of any of the preceding embodiments further comprising one or more active agents.

Embodiment 21 is the oral care composition (e.g., solution) of embodiment 20 wherein the one or more active agents comprise whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, proteins, or combinations thereof.

Embodiment 22 us the oral care composition (e.g., solution) of any of the preceding embodiments further comprising a flavoring agent.

Embodiment 23 is the oral care composition (e.g., solution) of any of the preceding embodiments further comprising a sweetener.

Embodiment 24 is the oral care composition (e.g., solution) of any of the preceding embodiments further comprising calcium cations.

Embodiment 25 is the oral care composition (e.g., solution) of embodiment 24 comprising a source of calcium cations selected from calcium chloride, calcium nitrate, calcium gluconate, calcium lactate gluconate, calcium acetate, hydrates thereof, and combinations thereof.

Embodiment 26 is the oral care composition (e.g., solution) of any of the preceding embodiments further comprising a surfactant.

Embodiment 27 is the oral care composition (e.g., solution) of embodiment 26 wherein the surfactant is an anionic surfactant.

Embodiment 28 is the oral care composition (e.g., solution) of embodiment 27 wherein the anionic surfactant is selected from polysorbate, glycerol, polyglycerol-based surfactant, and combinations thereof.

Embodiment 29 is the oral care composition (e.g., solution) of any of the preceding embodiments which does not stain teeth.

Embodiment 30 is the oral care composition (e.g., solution) of embodiment 29, which when combined 3:1 with a 1% phosphate composition (e.g., solution) and exposing it to a blue LED light with wavelength of 430-480 nm and output of approximately 1500 mW/cm$^2$ for 20 seconds (to see whether the mixture turned forms a dark (e.g., black, brown, or grey) precipitate).

Embodiment 31 is the oral care composition (e.g., solution) of any of the preceding embodiments which is shelf stable for at least 6 months, or at least 1 year.

Embodiment 32 is a method of providing fluoride to a patient's tooth surface, the method comprising applying the aqueous oral care one-part composition (e.g., solution) of any of the preceding embodiments to the patient's tooth surface.

Embodiment 33 is a method of reducing the incidence of dental caries (e.g., by preventing or arresting dental caries) in a patient in need thereof, the method comprising applying an aqueous oral care one-part composition (e.g., solution) of any of embodiments 1 through 31 to the patient's tooth surface.

Embodiment 34 is a method of reducing dentin sensitivity and/or root sensitivity (e.g., during cavity treatment and/or on an exposed root) in a patient in need thereof, the method comprising applying an aqueous oral care one-part composition (e.g., solution) of any of embodiments 1 through 31 to the patient's tooth surface.

Embodiment 35 is a method of treating a patient's tooth surface, the method comprising applying an aqueous oral care one-part composition (e.g., solution) of any of embodiments 1 through 31 to the patient's tooth surface.

Embodiment 36 is the method of any of embodiments 32 through 35 wherein the patient's tooth surface comprises enamel, dentin, cementum, root, or combinations thereof.

Embodiment 37 is the method of any of embodiments 32 through 36 wherein applying comprises painting the oral care composition (e.g., solution) on the patient's tooth surface.

Embodiment 38 is the method of any of embodiments 32 through 37 wherein applying comprises dispensing the oral care composition (e.g., solution) into a dental tray (e.g., an orthodontic aligner treatment tray) and attaching the tray having the oral care solution therein to the patient's tooth surface.

Embodiment 39 is the method of any of embodiments 32 through 38 wherein the oral care composition (e.g., solution) is subsequently dried (e.g., using flowing air) after being applied to the tooth surface.

Embodiment 40 is the method of any of embodiments 32 through 39 wherein water is subsequently applied to the oral care composition (e.g., solution) after being applied to the tooth surface to form a precipitate thereon (i.e., on the tooth surface).

Embodiment 41 is the method of any of embodiments 32 through 39 wherein saliva is subsequently allowed to contact the oral care composition (e.g., solution) on the tooth surface to form a precipitate thereon (i.e., on the tooth surface).

Embodiment 42 is the method of any of embodiments 32 through 41 further comprising placing a dental restorative on the tooth surface having the oral care composition (e.g., solution) applied thereto (either before or after the composition (e.g., solution) is dried, wiped off, rinsed off, and/or a precipitate is formed on the tooth surface).

Embodiment 43 is the method of embodiment 42 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 44 is a kit comprising an aqueous oral care one-part composition (e.g., solution) of any one of embodiments 1 through 31 and an applicator (e.g., dental brush, cotton tip swab).

Embodiment 45 is the kit of embodiment 44 wherein the oral care composition (e.g., solution) is provided in individual sealed unit dose containers.

Embodiment 46 is the kit of embodiment 44 wherein the oral care composition (e.g., solution) is provided in a multi-dose container.

Embodiment 47 is the kit of any of embodiments 44 to 46 wherein the applicator is integrated into the container having the oral care composition (e.g., solution) therein.

Embodiment 48 is the kit of any of embodiments 44 to 47 further comprising a dental restorative.

Embodiment 49 is the kit of embodiment 48 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 50 is the kit of any of embodiments 44 to 49 further comprising a tray, a dish, a well, or a pan.

Embodiment 51 is a method of making an aqueous oral care one-part composition (e.g., solution) of any one of embodiments 1 through 31 comprising combining a source of silver and a source of fluoride (which may be the same, e.g., AgF) in water and dissolving therein; and adding a source of thiocyanate (and optionally a source of iodide) and dissolving therein to form an aqueous oral care composition (e.g., solution).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

TABLE 1

Materials

| Description | Source | Location |
|---|---|---|
| Silver fluoride (AgF) | Oakwood Chemical | West Columbia, SC |
| Ammonium iodide ($NH_4I$) | Honeywell Specialty Chemical | Seelze, Germany |
| Ammonium thiocyanate ($NH_4SCN$) | Alfa Aesar | Ward Hill, MA |
| Guanidinium thiocyanate | Alfa Aesar | Ward Hill, MA |
| Disodium hydrogen citrate sesquihydrate | Alfa Aesar | Ward Hill, MA |
| Sodium carbonate | EMD | Gibbstown, NJ |
| Potassium phosphate monobasic | Sigma Aldrich | St Louis, MO |
| Ammonium chloride ($NH_4Cl$) | VWR | West Chester, PA |
| Potassium sulfate | J.T. Baker | Phillipsburg, NJ |
| Silver iodide | Sigma Aldrich | St Louis, MO |
| Silver diamine fluoride solution 38%, commercially available as ADVANTAGE ARREST silver diamine fluoride | Elevate Oral Care | West Palm Beach, FL |

Example Preparation

The general sample preparation procedure was as follows. Exact percent quantities are described in the tables below. An amount of 0.5 gram of the silver compound was added to an appropriately sized plastic tube. The full amount of water (described in tables below) was added to the container to dissolve the silver compound. The remaining component(s) were added to the silver compound solution. Initially, this addition caused a precipitate to occur. For examples of the present disclosure, the continued addition of the full amount of the remaining components caused the precipitate to re-dissolve, as the one-part composition (e.g., solution) was prepared. For comparative examples, the continued addition of the full amount of the remaining components did not re-dissolve the precipitate, the precipitate remained.

TABLE 2

Examples Ex-1 to Ex-5 and Comparative Example C-8; With $NH_4SCN$; Water Less than 57%

| Component | Ex-1 | Ex-2 | Ex-3 | Ex-4 | Ex-5 | C-8 |
|---|---|---|---|---|---|---|
| AgF | 22.7 | 20.8 | 19.2 | 17.9 | 16.7 | 14.3 |
| $NH_4SCN$ | 45.5 | 41.7 | 38.5 | 35.7 | 33.3 | 28.6 |
| $H_2O$ | 31.8 | 37.5 | 42.3 | 46.4 | 50.0 | 57.1 |
| Total (%) | 100 | 100 | 100 | 100 | 100 | 100 |
| Ag % | 19.3 | 17.7 | 16.4 | 15.2 | 14.2 | 12.1 |
| Fluoride % | 3.4 | 3.1 | 2.9 | 2.7 | 2.5 | 2.1 |
| Ag/SCN mole ratio | 0.30 | 0.30 | 0.30 | 0.30 | 0.30 | 0.30 |
| Precipitate formed initially | Yes | Yes | Yes | Yes | Yes | Yes |
| Precipitate dissolved with all chemicals in | Yes | Yes | Yes | Yes | Yes | No |

TABLE 3

Comparative Examples C-1 to C-7

| Components | C-1 | C-2 | C-3 | C-4 | C-5 | C-6 | C-7 |
|---|---|---|---|---|---|---|---|
| AgF | 16.7 | 16.7 | 16.7 | 16.7 | 16.7 | 18.4 | 18.5 |
| Disodium hydrogen citrate sesquihydrate | 50.0 | 0 | 0 | 0 | 0 | 0 | 0 |
| Sodium carbonate | 0 | 50.0 | 0 | 0 | 0 | 0 | 0 |
| Potassium phosphate monobasic | 0 | 0 | 50.0 | 0 | 0 | 0 | 0 |
| $NH_4Cl$ | 0 | 0 | 0 | 50.0 | 0 | 22.1 | 0 |
| $NH_4SCN$ | 0 | 0 | 0 | 0 | 0 | 0 | 22.2 |
| $NH_4I$ | 0 | 0 | 0 | 0 | 0 | 22.8 | 22.2 |
| Potassium sulfate | 0 | 0 | 0 | 0 | 50.0 | 0 | 0 |
| Deionized (DI) water | 33.3 | 33.3 | 33.3 | 33.3 | 33.3 | 36.8 | 37.0 |
| Total (%) | 100 | 100 | 100 | 100 | 100 | 100 | 100 |
| Ag % | 14.2 | 14.2 | 14.2 | 14.2 | 14.2 | 15.6 | 15.7 |
| Fluoride % | 2.5 | 2.5 | 2.5 | 2.5 | 2.5 | 2.8 | 2.8 |
| Ag/SCN mole ratio | 0 | 0 | 0 | 0 | 0 | 0 | 0.5 |
| Ag/I mole ratio | 0 | 0 | 0 | 0 | 0 | 0.92 | 0.95 |
| Precipitate formed initially | Yes | Yes | Yes | Yes | Yes | Yes | Yes |
| Precipitate dissolved with all chemicals in | No | No | No | No | No | No | No |

TABLE 4

Examples Ex-6 to Ex-8 and Comparative Example C-9; With $NH_4SCN$; Silver to Thiocyanate Mole Ratio Less than 0.37 to Dissolve Precipitate and Form a Solution

| Component | EX-6 | EX-7 | EX-8 | C-9 |
|---|---|---|---|---|
| AgF | 20.0 | 21.7 | 22.7 | 23.8 |
| $NH_4SCN$ | 40.0 | 39.1 | 45.5 | 38.1 |
| $H_2O$ | 40.0 | 39.1 | 31.8 | 38.1 |
| Total (%) | 100 | 100 | 100 | 100 |
| Ag/SCN mole ratio | 0.30 | 0.33 | 0.30 | 0.37 |
| Ag % | 17.0 | 18.5 | 19.3 | 20.2 |
| Fluoride % | 3.0 | 3.3 | 3.4 | 3.6 |
| Precipitate formed initially | Yes | Yes | Yes | Yes |
| Precipitate dissolved with all chemicals in | Yes | Yes | Yes | No |

TABLE 5

Example Ex-9

| Component | EX-9 |
|---|---|
| AgI | 0 |
| AgF | 18.5 |
| Guanidinium thiocyanate | 51.9 |
| DI water | 29.6 |
| Total % | 100 |
| Ag % | 15.7 |
| Total Fluoride % | 2.8 |

TABLE 5-continued

Example Ex-9

| Component | EX-9 |
|---|---|
| Precipitate formed initially | Yes |
| Precipitate dissolved with all chemicals in | Yes |

Light Sensitivity of Examples

The following examples demonstrated that compositions (e.g., solutions) of the present disclosure do not turn (discolor) to a dark color such as black, brown, or grey after (1) being precipitated with the addition of a buffer solution (to mimic saliva in the oral environment), and (2) exposure to light using 3M ELIPAR DEEPCURE-S LED curing light.

Comparative Example 10 (C-10)

An amount of 25 mg of silver diamine fluoride solution (ADVANTAGE ARREST silver diamine fluoride solution (38%)) was mixed with 40 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 mW/cm$^2$ for 20 seconds, the mixture turned black.

Example 10

An amount of 23 mg of EX-4 solution was mixed with 42 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 mW/cm$^2$ for 20 seconds, the mixture did NOT turn (discolor) to a dark color such as black, brown, or grey.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An aqueous oral care one-part composition comprising:
   silver cations;
   thiocyanate anions;
   fluoride anions; and
   water;
   wherein the molar ratio of silver to thiocyanate ions is less than 0.37:1, and water is less than 57.1 wt-%, based on the total weight of the composition.

2. The oral care one-part composition of claim 1 comprising:
   12.2-20 wt-% silver cations; and
   2.0-4.0 wt-% fluoride anions;
   wherein the weight percentages are based on the total weight of the composition;
   wherein the molar ratio of silver to thiocyanate ions is at least 0.1:1 and less than 0.37:1; and
   wherein the oral care composition forms a precipitate upon contact with additional water or saliva.

3. The oral care one-part composition of claim 1 or 2 comprising:
   12.2-20 wt-% silver cations;
   thiocyanate anions; and
   2.2-3.5 wt-% fluoride anions.

4. The oral care one-part composition of claim 1:
   a source of silver cations selected from silver fluoride, silver chloride, silver nitrate, silver iodide, silver diamine fluoride, and combinations thereof; and
   a source of fluoride anions selected from silver fluoride, silver diamine fluoride, sodium fluoride, ammonium fluoride, potassium fluoride, amine fluoride, and combinations thereof.

5. The oral care one-part composition of claim 1 comprising a source of thiocyanate anions selected from ammonium thiocyanate, sodium thiocyanate, potassium thiocyanate, guanidinium thiocyanate, and combinations thereof.

6. A method of providing fluoride to a patient's tooth surface, the method comprising applying the aqueous oral care one-part composition of claim 1.

7. A method of reducing the incidence of dental caries in a patient in need thereof, the method comprising applying an aqueous oral care one-part composition of claim 1 to the patient's tooth surface.

8. A method of reducing dentin sensitivity and/or root sensitivity in a patient in need thereof, the method comprising applying an aqueous oral care one-part composition of claim 1 to the patient's tooth surface.

9. A method of treating a patient's tooth surface, the method comprising:
   applying an aqueous oral care one-part composition to the patient's tooth surface; wherein the aqueous oral care one-part composition comprises: silver cations; thiocyanate anions; fluoride anions; and water; and
   optionally, applying a dental restorative to the treated tooth surface.

10. A kit comprising an aqueous oral care one-part composition of claim 1 and an applicator.

* * * * *